(12) United States Patent
Fuerderer (10) Patent No.: US 11,051,862 B2
(45) Date of Patent: *Jul. 6, 2021

(54) DEVICE FOR STRAIGHTENING AND STABILIZING THE VERTEBRAL COLUMN

(71) Applicant: DePuy Synthes Products, Inc., Raynham, MA (US)

(72) Inventor: Sebastian Fuerderer, Mainz (DE)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/124,282

(22) Filed: Sep. 7, 2018

(65) Prior Publication Data

US 2019/0008566 A1 Jan. 10, 2019

Related U.S. Application Data

(60) Continuation of application No. 15/833,011, filed on Dec. 6, 2017, now Pat. No. 10,357,291, which is a (Continued)

(30) Foreign Application Priority Data

Nov. 3, 2001 (DE) .................................. 10154163.5

(51) Int. Cl.
*A61B 17/70* (2006.01)
*A61B 17/88* (2006.01)
(Continued)

(52) U.S. Cl.
CPC ...... *A61B 17/7097* (2013.01); *A61B 17/8858* (2013.01); *A61M 25/10* (2013.01);
(Continued)

(58) Field of Classification Search
CPC ..... A61B 17/7097–7098; A61B 17/885–8858; A61F 2/44; A61F 2/441; A61F 2/4611; A61F 2002/444; A61F 2/46
See application file for complete search history.

(56) References Cited

U.S. PATENT DOCUMENTS 2,381,050 A 8/1945 Hardinge
3,701,703 A 10/1972 Zimmer et al.
(Continued)

FOREIGN PATENT DOCUMENTS

CN 102727309 B 11/2014
DE 9415039 U1 11/1994
(Continued)

OTHER PUBLICATIONS

**Cotten, Anne., MD., et al. "Percutaneous Vertebroplasty for Osteolytic Metastases and Myeloma: Effects of the Percentage of Lesion Filling and the Leakage of Methyl Methacrylate at Clinical Follow-up"., Radiology 1996; 200:525-530.
(Continued)

*Primary Examiner* — Eduardo C Robert
*Assistant Examiner* — Michelle C Eckman
(74) *Attorney, Agent, or Firm* — Nutter McClennen & Fish LLP (57) ABSTRACT

A device for straightening and stabilizing the vertebral column, particularly for stabilizing broken vertebrae, includes a supporting implant which is plastically expandable by internal pressure. The supporting implant can be placed into the interior of a vertebral body which has been fractured under compression or between adjacent vertebral bodies. A pressure balloon to which pressure fluid can be admitted may be arranged in the interior of the supporting implant for producing the internal pressure.

16 Claims, 2 Drawing Sheets

Related U.S. Application Data continuation of application No. 15/044,367, filed on Feb. 16, 2016, now Pat. No. 9,861,401, which is a continuation of application No. 13/924,881, filed on Jun. 24, 2013, now Pat. No. 9,295,502, which is a continuation of application No. 12/268,215, filed on Nov. 10, 2008, now Pat. No. 8,491,591, which is a division of application No. 10/286,458, filed on Nov. 1, 2002, now abandoned.

(51) Int. Cl.
*A61M 25/10* (2013.01)
*A61B 17/00* (2006.01)
*A61B 17/02* (2006.01)

(52) U.S. Cl.
CPC ........... *A61B 2017/00539* (2013.01); *A61B 2017/00557* (2013.01); *A61B 2017/0256* (2013.01); *A61M 2025/1004* (2013.01); *A61M 2210/02* (2013.01)

(56) References Cited

U.S. PATENT DOCUMENTS

| | | |
|---|---|---|
| 4,055,029 A | 10/1977 | Kalbow |
| 4,573,448 A | 3/1986 | Kambin |
| 4,646,738 A | 3/1987 | Trott |
| 4,678,459 A | 7/1987 | Onik et al. |
| 4,820,305 A | 4/1989 | Harms et al. |
| 4,820,349 A | 4/1989 | Saab |
| 4,863,430 A | 9/1989 | Klyce et al. |
| 4,888,146 A | 12/1989 | Dandeneau |
| 4,969,888 A * | 11/1990 | Scholten ............ A61B 17/8855 606/60 |
| 4,976,725 A | 12/1990 | Chin et al. |
| 5,041,114 A | 8/1991 | Chapman et al. |
| 5,059,193 A * | 10/1991 | Kuslich ............... A61F 2/4455 606/247 |
| 5,080,662 A | 1/1992 | Paul |
| 5,108,404 A | 4/1992 | Scholten et al. |
| 5,192,326 A | 3/1993 | Bao et al. |
| 5,195,541 A | 3/1993 | Obenchain |
| 5,285,795 A | 2/1994 | Ryan et al. |
| 5,342,298 A | 8/1994 | Michaels et al. |
| 5,390,683 A * | 2/1995 | Pisharodi ............. A61F 2/442 128/898 |
| 5,395,317 A | 3/1995 | Kambin |
| 5,439,464 A | 8/1995 | Shapiro |
| 5,443,496 A | 8/1995 | Schwartz et al. |
| 5,496,365 A * | 3/1996 | Sgro ...................... A61F 2/844 606/191 |
| 5,529,580 A | 6/1996 | Kusunoki et al. |
| 5,540,706 A | 7/1996 | Aust et al. |
| 5,549,679 A | 8/1996 | Kuslich |
| 5,569,290 A | 10/1996 | McAfee |
| 5,591,187 A | 1/1997 | Dekel |
| 5,599,301 A | 2/1997 | Jacobs et al. |
| 5,601,569 A | 2/1997 | Pisharodi |
| 5,601,593 A | 2/1997 | Freitag |
| 5,662,300 A | 9/1997 | Michelson |
| 5,674,277 A | 10/1997 | Freitag |
| 5,688,222 A | 11/1997 | Hluchy et al. |
| 5,693,100 A | 12/1997 | Pisharodi |
| 5,707,390 A | 1/1998 | Bonutti |
| 5,730,754 A | 3/1998 | Obenchain |
| 5,733,242 A | 3/1998 | Rayburn et al. |
| 5,735,792 A | 4/1998 | Vanden Hoek et al. |
| 5,759,191 A | 6/1998 | Barbere |
| 5,792,300 A | 8/1998 | Inderbitzen et al. |
| 5,820,623 A | 10/1998 | Ng |
| 5,827,289 A | 10/1998 | Reiley et al. |
| 5,885,300 A | 3/1999 | Tokuhashi et al. |
| 5,893,850 A | 4/1999 | Cachia |
| 5,894,369 A | 4/1999 | Akiba et al. |
| 5,899,425 A | 5/1999 | Corey, Jr. et al. |
| 5,954,635 A | 9/1999 | Foley et al. |
| 5,972,015 A * | 10/1999 | Scribner ............ A61B 10/025 604/20 |
| 6,019,793 A | 2/2000 | Perren et al. |
| 6,033,105 A | 3/2000 | Barker et al. |
| 6,053,907 A | 4/2000 | Zirps |
| 6,063,021 A | 5/2000 | Hossain et al. |
| 6,066,154 A * | 5/2000 | Reiley ................ A61B 17/7097 606/192 |
| 6,096,038 A | 8/2000 | Michelson |
| 6,110,182 A | 8/2000 | Mowlai-Ashtiani |
| 6,127,597 A * | 10/2000 | Beyar ................ A61B 17/7266 606/86 R |
| 6,149,651 A | 11/2000 | Drewry et al. |
| 6,179,856 B1 | 1/2001 | Barbere |
| 6,183,503 B1 | 2/2001 | Hart et al. |
| 6,200,322 B1 | 3/2001 | Branch et al. |
| 6,200,347 B1 | 3/2001 | Anderson et al. |
| 6,217,509 B1 | 4/2001 | Foley et al. |
| 6,234,961 B1 | 5/2001 | Gray |
| 6,235,043 B1 | 5/2001 | Reiley et al. |
| 6,241,734 B1 * | 6/2001 | Scribner ............ A61B 17/8816 606/93 |
| 6,245,107 B1 | 6/2001 | Ferree |
| 6,248,110 B1 * | 6/2001 | Reiley ................ A61B 10/025 606/192 |
| 6,283,966 B1 | 9/2001 | Houfburg |
| 6,286,179 B1 | 9/2001 | Byrne |
| 6,296,644 B1 | 10/2001 | Saurat et al. |
| 6,306,177 B1 | 10/2001 | Felt et al. |
| 6,322,498 B1 | 11/2001 | Gravenstein et al. |
| 6,332,894 B1 * | 12/2001 | Stalcup ................. A61F 2/4465 623/17.11 |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,395,007 B1 * | 5/2002 | Bhatnagar .......... A61B 17/8816 606/94 |
| 6,395,032 B1 | 5/2002 | Gauchet |
| 6,440,138 B1 | 8/2002 | Reiley et al. |
| 6,447,446 B1 | 9/2002 | Smith et al. |
| 6,468,289 B1 | 10/2002 | Bonutti |
| 6,478,800 B1 | 11/2002 | Fraser et al. |
| 6,494,883 B1 * | 12/2002 | Ferree ...................... A61F 2/28 606/247 |
| 6,558,390 B2 | 5/2003 | Cragg |
| 6,558,407 B1 | 5/2003 | Ivanko et al. |
| 6,575,899 B1 | 6/2003 | Foley et al. |
| 6,575,979 B1 * | 6/2003 | Cragg ................... A61B 17/1671 606/279 |
| 6,579,281 B2 | 6/2003 | Palmer et al. |
| 6,582,467 B1 * | 6/2003 | Teitelbaum ............ A61F 2/4465 623/17.11 |
| 6,613,054 B2 | 9/2003 | Scribner et al. |
| 6,620,162 B2 * | 9/2003 | Kuslich ............... A61B 17/7095 222/200 |
| 6,626,830 B1 | 9/2003 | Califiore et al. |
| 6,632,235 B2 | 10/2003 | Weikel et al. |
| 6,648,915 B2 | 11/2003 | Sazy |
| 6,663,647 B2 | 12/2003 | Reiley et al. |
| 6,676,597 B2 | 1/2004 | Guenst et al. |
| 6,679,886 B2 * | 1/2004 | Weikel ............... A61B 17/1671 606/167 |
| 6,688,564 B2 | 2/2004 | Salvermoser et al. |
| 6,706,069 B2 * | 3/2004 | Berger ............... A61B 17/8855 623/17.12 |
| 6,716,216 B1 | 4/2004 | Boucher et al. |
| 6,719,761 B1 | 4/2004 | Reiley et al. |
| 6,719,773 B1 * | 4/2004 | Boucher ............... A61B 17/68 606/192 |
| 6,726,691 B2 | 4/2004 | Osorio et al. |
| 6,733,532 B1 | 5/2004 | Gauchet et al. |
| 6,740,093 B2 | 5/2004 | Hochschuler et al. |
| 6,758,809 B2 | 7/2004 | Briscoe et al. |
| 6,808,505 B2 | 10/2004 | Kadan |
| 6,863,672 B2 | 3/2005 | Reiley et al. |
| 6,887,198 B2 | 5/2005 | Phillips et al. |

(56) References Cited

U.S. PATENT DOCUMENTS

| | | | |
|---|---|---|---|
| 6,899,716 B2* | 5/2005 | Cragg | A61B 17/1671 606/86 R |
| 6,899,719 B2 | 5/2005 | Reiley et al. | |
| 6,923,813 B2* | 8/2005 | Phillips | A61B 17/1604 606/192 |
| 6,981,981 B2 | 1/2006 | Reiley et al. | |
| 6,983,930 B1 | 1/2006 | La Mendola et al. | |
| 7,025,771 B2 | 4/2006 | Kuslich et al. | |
| 7,044,954 B2 | 5/2006 | Reiley et al. | |
| 7,087,058 B2 | 8/2006 | Cragg | |
| 7,097,648 B1 | 8/2006 | Globerman et al. | |
| 7,104,986 B2 | 9/2006 | Hovda et al. | |
| 7,108,714 B1 | 9/2006 | Becker | |
| 7,112,216 B2 | 9/2006 | Gregorich | |
| 7,137,949 B2 | 11/2006 | Scirica et al. | |
| 7,153,307 B2 | 12/2006 | Scribner et al. | |
| 7,166,121 B2 | 1/2007 | Reiley et al. | |
| 7,182,731 B2 | 2/2007 | Nguyen et al. | |
| 7,226,481 B2 | 6/2007 | Kuslich | |
| 7,241,303 B2 | 7/2007 | Reiss et al. | |
| 7,261,720 B2 | 8/2007 | Stevens et al. | |
| 7,341,556 B2 | 3/2008 | Shalman | |
| 7,434,325 B2 | 10/2008 | Foley et al. | |
| 7,591,790 B2 | 9/2009 | Pflueger | |
| 7,594,888 B2 | 9/2009 | Raymond et al. | |
| 7,618,431 B2 | 11/2009 | Roehm, III et al. | |
| 7,636,596 B2 | 12/2009 | Solar | |
| 7,637,905 B2 | 12/2009 | Saadat et al. | |
| 7,641,659 B2 | 1/2010 | Emstad et al. | |
| 7,682,378 B2* | 3/2010 | Truckai | A61B 17/1615 606/279 |
| 7,771,384 B2 | 8/2010 | Ravo | |
| 7,794,456 B2 | 9/2010 | Sharps et al. | |
| 7,811,303 B2 | 10/2010 | Fallin et al. | |
| 7,931,579 B2 | 4/2011 | Bertolero et al. | |
| 7,946,981 B1 | 5/2011 | Cubb | |
| 7,951,141 B2 | 5/2011 | Sharps et al. | |
| 7,959,564 B2 | 6/2011 | Ritland | |
| 7,988,623 B2 | 8/2011 | Pagliuca et al. | |
| 8,007,492 B2 | 8/2011 | DiPoto et al. | |
| 8,038,606 B2 | 10/2011 | Otawara | |
| 8,043,381 B2 | 10/2011 | Hestad et al. | |
| 8,062,218 B2 | 11/2011 | Sebastian et al. | |
| 8,062,368 B2* | 11/2011 | Heinz | A61F 2/441 623/17.11 |
| 8,092,464 B2 | 1/2012 | McKay | |
| 8,096,944 B2 | 1/2012 | Harrel | |
| 8,202,216 B2 | 6/2012 | Melkent et al. | |
| 8,236,006 B2 | 8/2012 | Hamada | |
| 8,262,609 B2* | 9/2012 | Sapida | A61B 17/8855 604/103.01 |
| 8,333,690 B2 | 12/2012 | Ikeda | |
| 8,360,970 B2 | 1/2013 | Mangiardi | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,435,174 B2 | 5/2013 | Cropper et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,491,591 B2* | 7/2013 | Furderer | A61B 17/7097 606/92 |
| 8,518,087 B2 | 8/2013 | Lopez et al. | |
| 8,529,628 B2 | 9/2013 | Marino et al. | |
| 8,535,220 B2 | 9/2013 | Mondschein | |
| 8,556,809 B2 | 10/2013 | Vijayanagar | |
| 8,585,726 B2 | 11/2013 | Yoon et al. | |
| 8,602,979 B2 | 12/2013 | Kitano | |
| 8,622,894 B2 | 1/2014 | Banik et al. | |
| 8,636,655 B1 | 1/2014 | Childs | |
| 8,690,764 B2 | 4/2014 | Clark et al. | |
| 8,721,536 B2 | 5/2014 | Marino et al. | |
| 8,740,779 B2 | 6/2014 | Yoshida | |
| 8,784,421 B2 | 7/2014 | Carrison et al. | |
| 8,821,378 B2 | 9/2014 | Morgenstern Lopez et al. | |
| 8,834,507 B2 | 9/2014 | Mire et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,894,573 B2 | 11/2014 | Loftus et al. | |
| 8,894,653 B2 | 11/2014 | Solsberg et al. | |
| 8,900,304 B1* | 12/2014 | Alobaid | A61B 17/7097 606/92 |
| 8,926,502 B2 | 1/2015 | Levy et al. | |
| 8,932,207 B2 | 1/2015 | Greenburg et al. | |
| 8,932,360 B2 | 1/2015 | Womble et al. | |
| 8,936,605 B2 | 1/2015 | Greenberg | |
| 8,974,381 B1 | 3/2015 | Lovell et al. | |
| 8,986,199 B2 | 3/2015 | Weisenburgh, II et al. | |
| 8,992,580 B2 | 3/2015 | Bar et al. | |
| 9,028,522 B1 | 5/2015 | Prado | |
| 9,050,146 B2 | 6/2015 | Woolley et al. | |
| 9,055,936 B2 | 6/2015 | Mire et al. | |
| 9,072,431 B2 | 7/2015 | Adams et al. | |
| 9,078,562 B2 | 7/2015 | Poll et al. | |
| 9,126,023 B1* | 9/2015 | Sahatjian | A61M 25/10 |
| 9,131,948 B2 | 9/2015 | Fang et al. | |
| 9,144,374 B2 | 9/2015 | Maurice, Jr. | |
| 9,198,674 B2 | 12/2015 | Benson et al. | |
| 9,211,059 B2 | 12/2015 | Drach et al. | |
| 9,216,016 B2 | 12/2015 | Fiechter et al. | |
| 9,216,125 B2 | 12/2015 | Sklar | |
| 9,220,554 B2* | 12/2015 | O'Halloran | A61B 17/1671 |
| 9,232,935 B2 | 1/2016 | Brand et al. | |
| 9,247,997 B2 | 2/2016 | Stefanchik et al. | |
| 9,265,491 B2 | 2/2016 | Lins et al. | |
| 9,277,928 B2 | 3/2016 | Morgenstern Lopez | |
| 9,283,018 B1* | 3/2016 | Alobaid | A61B 17/8852 |
| 9,289,240 B2* | 3/2016 | Messerli | A61B 17/68 |
| 9,295,502 B2 | 3/2016 | Fuerderer | |
| 9,307,972 B2 | 4/2016 | Lovell et al. | |
| 9,320,419 B2 | 4/2016 | Kirma et al. | |
| RE46,007 E | 5/2016 | Banik et al. | |
| RE46,062 E | 7/2016 | James et al. | |
| 9,386,971 B1 | 7/2016 | Casey et al. | |
| 9,387,313 B2 | 7/2016 | Culbert et al. | |
| 9,414,828 B2 | 8/2016 | Abidin et al. | |
| 9,486,296 B2 | 11/2016 | Mire et al. | |
| 9,492,194 B2 | 11/2016 | Morgenstern Lopez et al. | |
| 9,510,853 B2 | 12/2016 | Aljuri et al. | |
| 9,526,401 B2 | 12/2016 | Saadat et al. | |
| 9,579,012 B2 | 2/2017 | Vazales et al. | |
| 9,585,761 B2* | 3/2017 | Teisen | A61F 2/441 |
| 9,603,510 B2 | 3/2017 | Ammirati | |
| 9,603,610 B2 | 3/2017 | Richter et al. | |
| 9,610,007 B2 | 4/2017 | Kienzle et al. | |
| 9,610,095 B2 | 4/2017 | To | |
| 9,629,521 B2 | 4/2017 | Ratnakar | |
| 9,655,605 B2 | 5/2017 | Serowski et al. | |
| 9,655,639 B2 | 5/2017 | Mark | |
| 9,668,643 B2 | 6/2017 | Kennedy, II et al. | |
| 9,675,235 B2 | 6/2017 | Lieponis | |
| 9,700,378 B2 | 7/2017 | Mowlai-Ashtiani | |
| 9,706,905 B2 | 7/2017 | Levy | |
| 9,770,339 B2* | 9/2017 | Greenhalgh | A61F 2/4455 |
| 9,861,401 B2 | 1/2018 | Fuerderer | |
| 10,357,291 B2* | 7/2019 | Fuerderer | A61B 17/7097 |
| 10,405,906 B2* | 9/2019 | O'Halloran | A61B 17/8855 |
| 10,405,907 B2* | 9/2019 | Druma | A61B 17/8855 |
| 2001/0012946 A1 | 8/2001 | MacKenzie et al. | |
| 2001/0041896 A1* | 11/2001 | Reiley | A61B 10/025 606/93 |
| 2002/0022762 A1 | 2/2002 | Beane et al. | |
| 2002/0022856 A1* | 2/2002 | Johnson | A61B 17/320016 606/185 |
| 2002/0026195 A1 | 2/2002 | Layne et al. | |
| 2002/0058947 A1* | 5/2002 | Hochschuler | A61B 17/7097 606/94 |
| 2002/0068974 A1* | 6/2002 | Kuslich | A61B 17/68 623/17.11 |

(56) References Cited

U.S. PATENT DOCUMENTS

| | | |
|---|---|---|
| 2002/0099384 A1* | 7/2002 | Scribner .............. A61B 17/1631 606/92 |
| 2002/0138020 A1 | 9/2002 | Pflueger |
| 2002/0156529 A1 | 10/2002 | Li et al. |
| 2002/0161373 A1* | 10/2002 | Osorio ................ A61B 17/1604 606/86 R |
| 2002/0177866 A1* | 11/2002 | Weikel ................. A61B 17/025 606/192 |
| 2003/0028251 A1* | 2/2003 | Mathews .............. A61M 25/10 623/17.16 |
| 2003/0033017 A1* | 2/2003 | Lotz ........................ A61F 2/441 623/17.16 |
| 2003/0050644 A1* | 3/2003 | Boucher ............ A61B 17/3472 606/90 |
| 2003/0050702 A1 | 3/2003 | Berger |
| 2003/0083555 A1 | 5/2003 | Hunt et al. |
| 2003/0088249 A1 | 5/2003 | Fuerderer |
| 2003/0130664 A1* | 7/2003 | Boucher ............ A61B 17/1631 606/86 R |
| 2003/0171744 A1 | 9/2003 | Leung et al. |
| 2003/0191474 A1 | 10/2003 | Cragg et al. |
| 2003/0220649 A1 | 11/2003 | Bao et al. |
| 2003/0220650 A1* | 11/2003 | Major ................. A61B 17/025 606/90 |
| 2004/0010315 A1* | 1/2004 | Song ........................ A61F 2/44 623/17.16 |
| 2004/0073308 A1 | 4/2004 | Kuslich et al. |
| 2004/0087994 A1* | 5/2004 | Suddaby ............ A61B 17/8858 606/190 |
| 2004/0097930 A1 | 5/2004 | Justis et al. |
| 2004/0098017 A1* | 5/2004 | Saab ................. A61B 17/8855 606/192 |
| 2004/0102774 A1* | 5/2004 | Trieu ................. A61B 17/7097 606/86 A |
| 2004/0122446 A1 | 6/2004 | Solar |
| 2004/0127992 A1 | 7/2004 | Serhan et al. |
| 2004/0143165 A1 | 7/2004 | Alleyne |
| 2004/0143330 A1 | 7/2004 | Sazy |
| 2004/0167625 A1 | 8/2004 | Beyar et al. |
| 2004/0210297 A1 | 10/2004 | Lin et al. |
| 2004/0215343 A1 | 10/2004 | Hochschuler et al. |
| 2004/0215344 A1 | 10/2004 | Hochschuler et al. |
| 2004/0220615 A1 | 11/2004 | Lin et al. |
| 2005/0070911 A1* | 3/2005 | Garrison .............. A61B 17/885 606/90 |
| 2005/0085692 A1 | 4/2005 | Kiehn et al. |
| 2005/0090848 A1 | 4/2005 | Adams |
| 2005/0131267 A1* | 6/2005 | Talmadge ............ A61B 10/025 600/3 |
| 2005/0131268 A1* | 6/2005 | Talmadge ............ A61B 10/025 600/3 |
| 2005/0131269 A1* | 6/2005 | Talmadge ............ A61B 10/025 600/3 |
| 2005/0143827 A1 | 6/2005 | Globerman et al. |
| 2005/0187570 A1 | 8/2005 | Nguyen et al. |
| 2005/0234498 A1* | 10/2005 | Gronemeyer ...... A61B 17/7098 606/192 |
| 2005/0256525 A1 | 11/2005 | Culbert et al. |
| 2005/0261683 A1* | 11/2005 | Veldhuizen ........ A61B 17/8852 623/17.11 |
| 2005/0278036 A1* | 12/2005 | Leonard .................... A61F 2/44 623/23.47 |
| 2006/0079905 A1 | 4/2006 | Beyar et al. |
| 2006/0100706 A1* | 5/2006 | Shadduck ............ A61B 17/1617 623/17.11 |
| 2006/0149349 A1* | 7/2006 | Garbe .................. A61B 17/11 623/1.11 |
| 2006/0190083 A1 | 8/2006 | Amin et al. |
| 2006/0206118 A1 | 9/2006 | Kim et al. |
| 2006/0210605 A1 | 9/2006 | Chang et al. |
| 2006/0217795 A1 | 9/2006 | Besselink et al. |
| 2006/0235423 A1* | 10/2006 | Cantu ................. A61B 17/8858 606/90 |
| 2006/0271061 A1* | 11/2006 | Beyar ................ A61B 1/00071 606/105 |
| 2006/0293750 A1* | 12/2006 | Sherman .................... A61F 2/44 623/17.12 |
| 2007/0032791 A1* | 2/2007 | Greenhalgh ....... A61B 17/8858 606/279 |
| 2007/0043440 A1* | 2/2007 | William .............. A61B 17/8858 623/17.11 |
| 2007/0055259 A1 | 3/2007 | Norton et al. |
| 2007/0055266 A1 | 3/2007 | Osorio et al. |
| 2007/0055267 A1 | 3/2007 | Osorio et al. |
| 2007/0055276 A1* | 3/2007 | Edidin .............. A61B 17/8855 606/92 |
| 2007/0055280 A1 | 3/2007 | Osorio et al. |
| 2007/0055284 A1 | 3/2007 | Osorio et al. |
| 2007/0055285 A1 | 3/2007 | Osorio et al. |
| 2007/0093899 A1* | 4/2007 | Dutoit ................. A61B 17/686 623/17.11 |
| 2007/0129634 A1 | 6/2007 | Hickey et al. |
| 2007/0149975 A1 | 6/2007 | Oliver et al. |
| 2007/0173939 A1* | 7/2007 | Kim ................... A61B 17/1633 623/17.11 |
| 2007/0173940 A1 | 7/2007 | Hestad ...................... A61F 2/44 623/17.12 |
| 2007/0203396 A1 | 8/2007 | McCutcheon et al. |
| 2007/0219634 A1 | 9/2007 | Greenhalgh et al. |
| 2007/0225556 A1 | 9/2007 | Ortiz et al. |
| 2007/0244485 A1* | 10/2007 | Greenhalgh ............ A61F 2/446 606/86 R |
| 2007/0255285 A1* | 11/2007 | Trieu ................. A61B 17/7097 606/86 R |
| 2007/0255406 A1* | 11/2007 | Trieu ................. A61B 17/7097 623/17.11 |
| 2007/0260113 A1 | 11/2007 | Otawara |
| 2007/0270956 A1* | 11/2007 | Heinz ........................ A61F 2/44 623/17.11 |
| 2007/0282443 A1 | 12/2007 | Globerman et al. |
| 2008/0015621 A1 | 1/2008 | Emanuel |
| 2008/0033251 A1 | 2/2008 | Araghi |
| 2008/0071356 A1* | 3/2008 | Greenhalgh ....... A61B 17/8858 623/1.16 |
| 2008/0081951 A1 | 4/2008 | Frasier et al. |
| 2008/0086133 A1 | 4/2008 | Kuslich et al. |
| 2008/0188714 A1 | 8/2008 | McCaffrey |
| 2008/0249604 A1 | 10/2008 | Donovan et al. |
| 2009/0012618 A1* | 1/2009 | Ahrens .............. A61B 17/7094 623/17.12 |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0069850 A1 | 3/2009 | Fuerderer |
| 2009/0105543 A1 | 4/2009 | Miller et al. |
| 2009/0156898 A1 | 6/2009 | Ichimura |
| 2009/0187080 A1 | 7/2009 | Seex |
| 2009/0234457 A1* | 9/2009 | Lotz ........................ A61F 2/441 623/17.16 |
| 2009/0240111 A1 | 9/2009 | Kessler et al. |
| 2009/0287061 A1 | 11/2009 | Feigenbaum et al. |
| 2009/0299282 A1* | 12/2009 | Lau .................... A61B 17/8811 604/99.01 |
| 2009/0299373 A1* | 12/2009 | Sisken ............... A61B 17/7098 606/92 |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0286782 A1* | 11/2010 | Schaller ............. A61B 17/1642 623/17.12 |
| 2010/0312053 A1 | 12/2010 | Larsen |
| 2011/0028791 A1 | 2/2011 | Marino et al. |
| 2011/0054507 A1 | 3/2011 | Batten et al. |

(56) References Cited

U.S. PATENT DOCUMENTS

| | | |
|---|---|---|
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0137317 A1* | 6/2011 | O'Halloran ........ A61B 17/7097 606/92 |
| 2011/0295070 A1 | 12/2011 | Yasunaga |
| 2011/0319941 A1 | 12/2011 | Bar et al. |
| 2012/0010624 A1* | 1/2012 | O'Halloran ........ A61B 17/1671 606/94 |
| 2012/0010713 A1* | 1/2012 | O'Halloran ........ A61B 17/7097 623/17.12 |
| 2012/0041462 A1* | 2/2012 | Maeng ............... A61B 17/8855 606/185 |
| 2012/0041557 A1 | 2/2012 | Frigg |
| 2012/0095296 A1 | 4/2012 | Trieu et al. |
| 2012/0101338 A1 | 4/2012 | O'Prey et al. |
| 2012/0109139 A1* | 5/2012 | Steele .................... A61B 17/70 606/92 |
| 2012/0165941 A1 | 6/2012 | Rabiner et al. |
| 2012/0179162 A1* | 7/2012 | Tilson ............... A61B 17/7097 606/94 |
| 2012/0197319 A1* | 8/2012 | Auyoung ........... A61B 17/7097 606/86 R |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0239047 A1* | 9/2012 | Linderman ........ A61B 17/8805 606/93 |
| 2012/0290095 A1* | 11/2012 | Diwan .................... A61F 2/441 623/17.16 |
| 2012/0298820 A1 | 11/2012 | Manolidis |
| 2012/0316400 A1 | 12/2012 | Vijayanagar |
| 2013/0018467 A1* | 1/2013 | Suh ........................... A61F 2/44 623/17.16 |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0197563 A1* | 8/2013 | Saab ..................... A61M 29/02 606/191 |
| 2013/0218164 A1* | 8/2013 | Mueller ............. A61B 17/8819 606/93 |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0310877 A1 | 11/2013 | Fuerderer |
| 2014/0046334 A1* | 2/2014 | Schaus ............... A61B 17/8805 606/93 |
| 2014/0066940 A1 | 3/2014 | Fang et al. |
| 2014/0074170 A1 | 3/2014 | Mertens et al. |
| 2014/0114368 A1* | 4/2014 | Lin .................... A61B 17/7097 606/86 R |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0207193 A1* | 7/2014 | Druma ............... A61B 17/8855 606/279 |
| 2014/0215736 A1 | 8/2014 | Gomez et al. |
| 2014/0249634 A1* | 9/2014 | Choi ...................... A61F 2/441 623/17.16 |
| 2014/0257489 A1 | 9/2014 | Warren et al. |
| 2014/0275799 A1 | 9/2014 | Schuele |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0065795 A1 | 3/2015 | Titus |
| 2015/0073218 A1 | 3/2015 | Ito |
| 2015/0094730 A1* | 4/2015 | Hayakawa ......... A61B 17/7097 606/93 |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0157898 A1 | 6/2016 | Fuerderer |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0310286 A1* | 10/2016 | McJunkin ............... A61F 2/441 |
| 2016/0353978 A1 | 12/2016 | Miller et al. |
| 2017/0003493 A1 | 1/2017 | Zhao |
| 2017/0007226 A1 | 1/2017 | Fehling |
| 2017/0014166 A1* | 1/2017 | Little ................. A61B 17/7258 |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2018/0153594 A1 | 6/2018 | Fuerderer |
| 2019/0269531 A1* | 9/2019 | Cornelis ............ A61B 17/7097 |
| 2019/0269892 A1* | 9/2019 | Tilson ................ A61B 17/8833 |

FOREIGN PATENT DOCUMENTS

| | | |
|---|---|---|
| DE | 195 08 805 A1 | 11/1996 |
| DE | 29916026 U1 | 11/1999 |
| EP | 0 537 116 A1 | 4/1993 |
| EP | 0 493 789 B1 | 3/1997 |
| EP | 0 807 415 A2 | 11/1997 |
| GB | 2481727 A | 1/2012 |
| JP | 11-076246 A | 3/1999 |
| WO | 96/29014 A1 | 9/1996 |
| WO | 97/16219 A1 | 5/1997 |
| WO | 98/38918 A1 | 9/1998 |
| WO | 98/56301 A1 | 12/1998 |
| WO | 99/24223 A1 | 5/1999 |
| WO | 00/44319 A1 | 8/2000 |
| WO | 2001/056490 A1 | 8/2001 |
| WO | 01/76514 A2 | 10/2001 |
| WO | 2001/089371 A1 | 11/2001 |
| WO | 2002/002016 A1 | 1/2002 |
| WO | 02/43628 A1 | 6/2002 |
| WO | 02/076678 A1 | 10/2002 |
| WO | 03/007853 A1 | 1/2003 |
| WO | 2004/103430 A2 | 12/2004 |
| WO | 2005/048856 A1 | 6/2005 |
| WO | 2008/121162 A1 | 10/2008 |
| WO | 2009/033207 A1 | 3/2009 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2016/111373 A1 | 7/2016 |

(56) References Cited

FOREIGN PATENT DOCUMENTS

| WO | 2016/131077 A1 | 8/2016 |
| WO | 2016/168673 A1 | 10/2016 |
| WO | 2017/006684 A1 | 1/2017 |
| WO | 2017/015480 A1 | 1/2017 |
| WO | 2017/083648 A1 | 5/2017 |

OTHER PUBLICATIONS

**Cotten, Anne, et al., "Preoperative Percutaneous Injection of Methyl Methacrylate and N-Butyl Cyanoacrylate in Vertebral Hemangiomas"; AJNR 17:137-142 (1996).
**European Search Report for Application No. 02024098.2, dated May 15, 2003 with an English Translations of the pertinent portions (101896-1387) (4 pages).
**Gangi, Afshin, et al., "Percutaneous Vertebroplasty Guided by a Combination of CT and Fluoroscopy"., AJNR 15:83-86, Jan. 1994.
**Japanese Office Action for Application No. 2002-346496, dated Nov. 25, 2008. Includes Japanese Search (18 pages).
**Jensen, Mary E, et al., "Percutaneous Polymethylmethacrylate Vertebroplasty in the Treatment of Osteoporotic Vertebral Body CompressionFractures: Technical Aspects"., AJNR: Nov. 18, 1997.
**Maciunas, Robert J., MD., "Endovascular Neurological Intervention"; American Association of Neurological Surgeons; 153-158.
International Search Report and Written Opinion for Application No. PCT/US2015/043554, dated Nov. 19, 2015 (8 pages).
International Search Report and Written Opinion for Application No. PCT/US2015/048485, dated Feb. 9, 2016. (16 pages).
International Search Report and Written Opinion for Application No. PCT/US2015/060978, dated Feb. 15, 2016 (8 pages).
Invitation to Pay Additional Fees for Application No. PCT/US2016/050022, dated Nov. 3, 2016 (2 pages).
International Search Report and Written Opinion for Application No. PCT/US2016/050022, dated Feb. 1, 2017 (19 pages).
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Jung, K, et al., "A hands-free region-of-interest selection interface for solo surgery with a wide-angle endoscope: preclinical proof of concept," Surg Endosc, 2017, v. 31, pp. 974-980.

* cited by examiner

DEVICE FOR STRAIGHTENING AND STABILIZING THE VERTEBRAL COLUMN

CROSS-REFERENCE TO RELATED APPLICATIONS

This application is a continuation of U.S. application Ser. No. 15/833,011 filed on Dec. 6, 2017. U.S. application Ser. No. 15/833,011 is a continuation of U.S. application Ser. No. 15/044,367 filed on Feb. 16, 2016 and now issued as U.S. Pat. No. 9,861,401. U.S. application Ser. No. 15/044,367 is a continuation of U.S. application Ser. No. 13/924,881 filed on Jun. 24, 2013 and now issued as U.S. Pat. No. 9,295,502. U.S. application Ser. No. 13/924,881 is a continuation of U.S. application Ser. No. 12/268,215 filed on Nov. 10, 2008 and now issued as U.S. Pat. No. 8,491,591. U.S. application Ser. No. 12/268,215 is a divisional of U.S. application Ser. No. 10/286,458 filed on Nov. 1, 2002 and now abandoned. U.S. application Ser. No. 10/286,458 claims priority to German Patent Application No. DE 101 54 163.5 filed Nov. 3, 2001. The entire contents of each of these applications is incorporated herein by reference.

BACKGROUND OF THE INVENTION

1. Field of the Invention

The present invention relates to a device for straightening and stabilizing the vertebral column, particularly for stabilizing broken vertebrae.

2. Description of the Related Art

Devices for straightening and stabilizing broken vertebrae are known to be used. These devices include a catheter which can be inserted into the interior of the vertebra through a duct drilled into the pedicle of the broken vertebra. A pressure line pushed through the catheter into the interior of the vertebra has at the end thereof an expandable pressure balloon which makes it possible to expand once again and return into its original shape a vertebra which has been compressed and possibly broken. The balloon which has subsequently been decompressed and pulled out together with the pressure line leaves a hollow space into which a bone filler material can be introduced through the catheter.

SUMMARY OF THE INVENTION

It is the primary object of the present invention to provide a novel device for stabilizing the vertebral column, particularly for straightening and stabilizing broken vertebrae, which makes it possible to achieve a higher degree of stabilization more quickly than by using the known devices, wherein the required operation is simpler.

In accordance with the present invention, the device for straightening and stabilizing the vertebral column is characterized by a supporting implant which is plastically expandable by internal pressure.

Such a supporting implant, which is preferably provided for being arranged in the interior of a vertebral body fractured under compression or also, for example, after an intervertebral disc resection for arrangement between adjacent vertebral bodies, can be easily moved to the implantation location because of its small dimensions. After the expansion has been effected, a preliminary stabilization is ensured immediately because the supporting implant maintains its final shape obtained during the plastic expansion. A filler material which is initially present in liquid form can be introduced under slight pressure into the created hollow space and can harden in the hollow space. Because of the action of the supporting implant, it is not necessary to wait until the filler material has hardened completely.

While mechanical tools for producing the internal pressure are conceivable, a preferred embodiment of the invention provides for a device which produces the internal pressure by means of a pressure fluid.

The pressure fluid can be introduced directly into the supporting implant, which requires that the supporting implant and the supply connections are pressure tight. However, in accordance with a preferred embodiment, a pressure balloon is provided which is arranged in the interior of the supporting implant and into which the pressure fluid can be introduced.

The expandable supporting implant may include a weakened wall, or a wall which is perforated in the manner of expanded metal and/or folded in the manner of a bellows.

This type of supporting implant can be expanded with relatively low internal pressure, wherein the stability of the expanded implant is reduced by the weakened or folded portions, however, the implant can still carry out a sufficient supporting function.

The wall of the expandable supporting implant may have weak portions and/or folds arranged in such a way that the supporting implant expands into a desired shape. For example, if such a supporting implant is arranged between adjacent vertebrae, the desired shape is approximately that of a parallelepiped.

In accordance with a preferred embodiment of the invention, the expandable supporting implant has an oblong shape so that it is suitable for being arranged at the implantation location by means of a catheter or a guide sleeve. In particular, the expandable supporting implant, and possibly the pressure balloon, may be placed in the manner of a stocking on a pressure line which can be introduced through the guide sleeve, wherein the pressure balloon is arranged between the supporting implant and the pressure line and, in the non-expanded state, forms a hose-type sleeve which surrounds the pressure line and which is connected at its ends in a pressure-tight manner by being placed around the circumference of the pressure line.

The pressure fluid is preferably not compressible, and a device for measuring the supplied amount of pressure fluid is provided. This makes it possible to control the degree of expansion through the supplied quantity.

In accordance with another advantageous embodiment of the invention, a monitoring device is provided which monitors changes over time of the fluid pressure and the supplied fluid quantity so that the pressure application can be interrupted when predetermined relative values of these changes are exceeded. Such a monitoring device prevents fluid which is under high pressure from being released into the body when the supporting implant is destroyed, for example, as a result of a material defect.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE INVENTION

Figures 1, 2, 5:
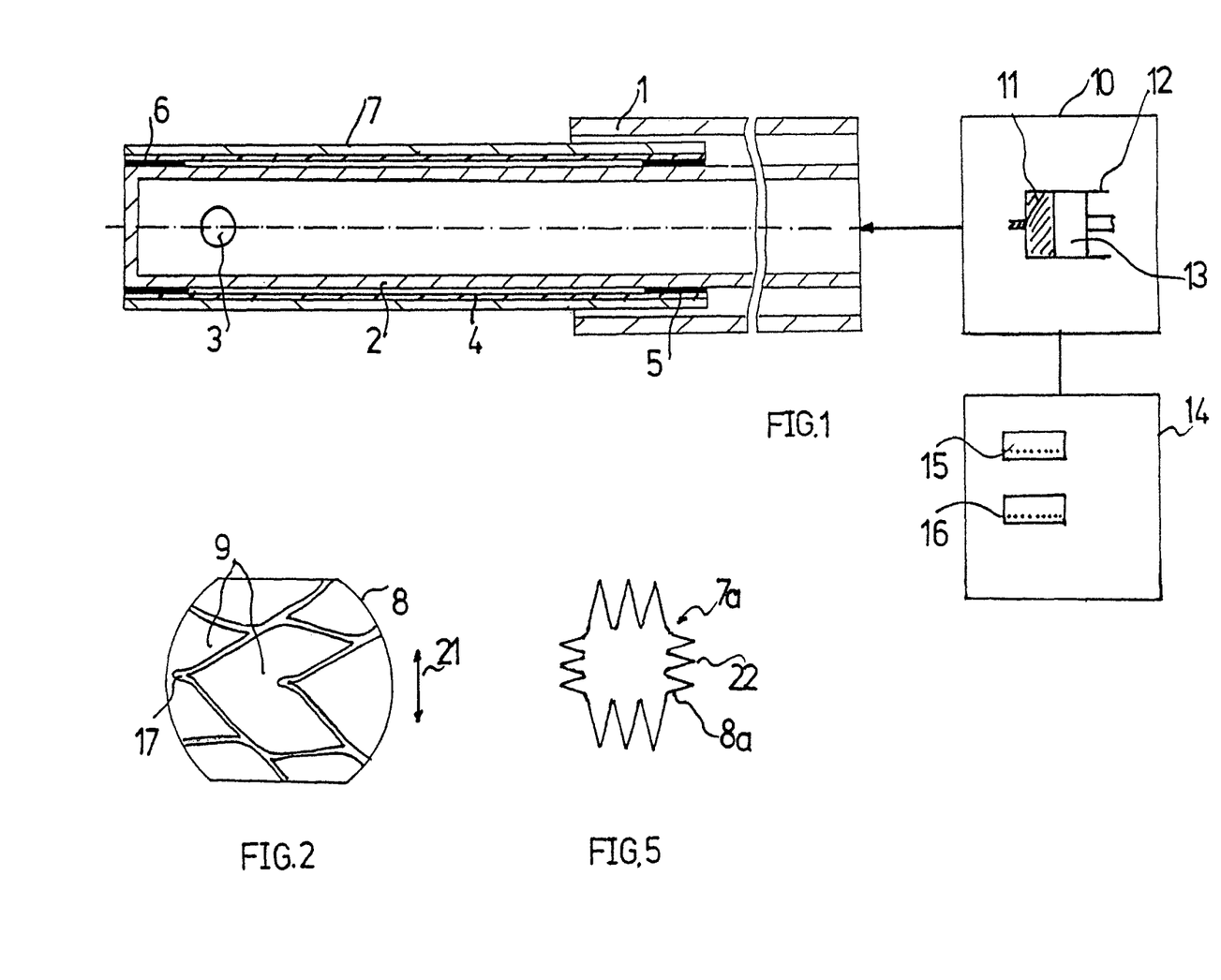
FIG. 1 is a schematic sectional view of a device according to the invention with a supporting implant placed on a pressure line.
FIG. 2 is an illustration of a detail of the supporting implant of FIG. 1.
FIG. 5 is an illustration of another embodiment of the supporting implant which can be used in a device of the invention.

FIG. 1 of the drawing shows a guide sleeve 1 and a pressure line 2 extending through the guide sleeve 1, wherein the pressure line 2 is provided with an opening 3 for releasing a pressure fluid.

An elastic hose-type sheath 4 is placed in the manner of a stocking and flush at the ends thereof on the circular cylindrical pressure line 2. The sheath 4 is glued in a pressure-tight manner at its ends to the circumference of the pressure line 2 at 5 and 6. Instead of providing a glued connection, it would also be possible to press the elastic sheath 4 at the ends thereof by means of rings against the pressure line.

A hollow-cylindrical supporting implant 7 is placed around the elastic sheath 4. As can be seen in FIG. 2, the cylindrical wall 8 of the implant 7 is a mesh-like material with openings 9, wherein wires of the mesh extend at an acute angle relative to each other. The wall 8 can be tangentially expanded in the manner of expanded metal in the direction of double arrow 21, so that the supporting implant 7 is radially expanded.

At its end opposite the sheath 4 or the supporting implant 7, the pressure line 2 is in connection with a schematically illustrated device 10 for supplying an incompressible pressure fluid 11, wherein this device 10 includes a pressure cylinder 12 and a piston 13. The piston 13 may be movable manually, preferably by means of a screw-type pressure gauge, or by means of a motor drive.

Reference numeral 14 denotes a schematically illustrated control and monitoring device which includes a pressure indicator 16 and a display 17 for the supplied quantity of pressure fluid.

Figure 3:
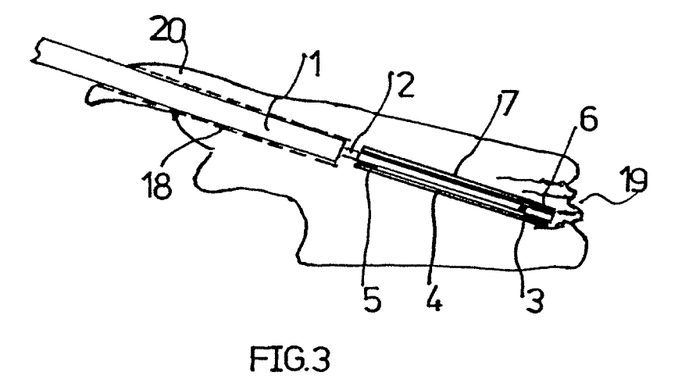
FIG. 3 is an illustration, on a smaller scale, showing the device of FIG. 1 inserted into a broken and compressed vertebral body.

The manner of operation of the device is shown in FIGS. 1 and 2 and shall now be explained in connection with FIGS. 3 and 4.

For stabilizing a broken vertebra, initially a duct 18 is drilled through the pedicle 20, wherein a catheter and a drilling tool extending through the catheter can be used for this purpose. As shown in FIGS. 3 and 4, the guide sleeve 1 is now placed in the duct 18 and the pressure fluid 2 with the supporting implant 7 can be forwardly pushed into the interior of the compressed vertebra which has compression folds at 19.

The incompressible pressure fluid 11 is pressed by means of the device 10 into the pressure line 2, the pressure fluid 11 emerges from the opening 3 and the elastic sheath 4 is expanded into a balloon. The expanding sheath or balloon 4 expands the supporting implant 7, as illustrated in FIG. 4, wherein the wall 8 of the supporting implant 7 is plastically deformed in the direction of arrow 21 shown in FIG. 2 and the acute angles between the mesh wires at 17 are widened.

The quantity of supplied pressure fluid during the expansion can be read at the display 17 of the control and monitoring device 14 and, thus, the extent of the achieved expansion can be determined. The expansion or supply of pressure fluid is stopped when a predetermined value of the supplied pressure fluid quantity has been reached.

The control and monitoring device 14 further ensures that the application of pressure is stopped immediately if the balloon 4 ruptures during the expansion, for example, due to a material defect, and pressure fluid is released from the vertebra; this is the case when the supplied pressure fluid quantity increases significantly over time, while the pressure stays constant or increases only slightly.

After the required expansion has been achieved, the pressure fluid is withdrawn through the opening 3 which is located near the lowest point of the balloon 4. The pressure line 2 with the empty pressure balloon or the empty sheath 4 can now be pulled back through the guide sleeve 1.

Figure 4:
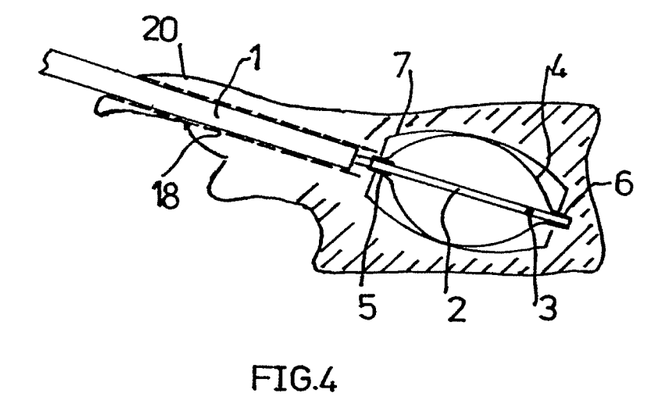
FIG. 4 shows the vertebral body of FIG. 3 which has been expanded by means of the device of FIG. 1.

The plastically deformed supporting implant 7 maintains its shape and supports the vertebra in such a way that it maintains the shape shown in FIG. 4 and the damage shown at 19 can heal. A filler material is introduced into the interior of the supporting implant.

FIG. 2 is a cross-sectional view of another embodiment of a supporting implant 7a according to the invention. The supporting implant 7a has in its wall 8a folds 22, wherein the folds on opposite sides have different lengths, so that the expanded implant has a rectangular shape in cross-section.

In the embodiment described above, a salt solution containing an x-ray contrast agent is used as the pressure fluid.

Of course, two of the above-described supporting implants can be and are usually inserted into a broken vertebra, wherein ducts are drilled in both pedicles for inserting a catheter.

While specific embodiments of the invention have been shown and described in detail to illustrate the inventive principles, it will be understood that the invention may be embodied otherwise without departing from such principles.

I claim:

1. A surgical method, comprising:
   inserting a sleeve into a portion of the vertebral column, the sleeve having a lumen extending therethrough;
   inserting a balloon through the lumen of the sleeve;
   filling the balloon with a fluid to expand the balloon within the portion of the vertebral column;
   inserting an implant through the lumen of the sleeve into the portion of the vertebral column, the implant being inserted through the same lumen as the balloon; and
   withdrawing the balloon from the portion of the vertebral column;
   wherein a portion of an inner surface of the implant is distanced from an outer surface of the balloon.

2. The method of claim 1, further comprising expanding the implant from a first configuration to a second configuration that is larger than the first configuration;
   wherein the implant is in the first configuration when inserted into the portion of the vertebral column and expanding the implant to the second configuration is performed while the implant is positioned within the portion of the vertebral column.

3. The method of claim 2, wherein the implant is expanded by introducing a filler into a hollow space within the implant.

4. The method of claim 3, wherein the filler is introduced in liquid form and subsequently hardens.

5. The method of claim 1, further comprising delivering a filler into an interior of the implant.

6. The method of claim 5, wherein the filler is introduced in liquid form and subsequently hardens.

7. The method of claim 5, wherein delivering the filler into the interior of the implant is performed after inserting the implant into the portion of the vertebral column.

8. The method of claim 1, further comprising withdrawing the fluid from the balloon prior to withdrawing the balloon from the portion of the vertebral column.

9. The method of claim 1, wherein filling the balloon with the fluid is performed after inserting the balloon into the portion of the vertebral column.

10. The method of claim 1, further comprising making an incision in a patient's skin and forming a duct to access the portion of the vertebral column.

11. The method of claim 1, wherein at least one of the balloon and the implant are inserted using a guide.

12. The method of claim 1, wherein the implant is formed from a mesh-like material.

13. The method of claim 1, wherein the implant has an oblong shape.

14. The method of claim 1, wherein the fluid filled into the balloon is incompressible.

15. The method of claim 1, further comprising monitoring a pressure of the fluid and a quantity of the fluid within the balloon to control expansion of the balloon.

16. A surgical method, comprising:
inserting a balloon through a lumen of a sleeve into a space within the vertebral column;
filling the balloon with a fluid to expand the balloon to distract the space;
inserting an implant through the lumen of the sleeve into the space to maintain the space in the distracted state, the implant being inserted through the same lumen as the balloon; and
withdrawing the balloon from the space;
wherein the space in the distracted state is larger than a maximum volume of the balloon, and
wherein a gap is formed between a portion of an inner surface of the implant and an outer surface of the balloon.

* * * * *